(12) United States Patent
Chang (10) Patent No.: US 8,206,712 B2
(45) Date of Patent: Jun. 26, 2012

(54) USE OF ANTI-IL-20 ANTIBODY FOR TREATING RHEUMATOID ARTHRITIS

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 11 days.

(21) Appl. No.: 12/829,697

(22) Filed: Jul. 2, 2010

(65) Prior Publication Data

US 2011/0002925 A1 Jan. 6, 2011

Related U.S. Application Data

(62) Division of application No. 12/246,715, filed on Oct. 7, 2008, now Pat. No. 7,837,994.

(51) Int. Cl.
*A61K 39/395* (2006.01)

(52) U.S. Cl. .............. 424/141.1; 424/130.1; 424/133.1; 514/1.1; 530/388.23; 530/387.3; 530/350; 530/351

(58) Field of Classification Search .................. None
See application file for complete search history.

(56) References Cited

U.S. PATENT DOCUMENTS

| | | | |
|---|---|---|---|
| 5,605,690 | A | 2/1997 | Jacobs et al. |
| 7,122,632 | B2 | 10/2006 | Foster et al. |
| 7,435,800 | B2 | 10/2008 | Chang |
| 7,611,705 | B2 | 11/2009 | Chang |
| 2002/0151532 | A1 | 10/2002 | Kagan et al. |
| 2003/0148955 | A1 | 8/2003 | Pluenneke |
| 2004/0235728 | A1 | 11/2004 | Stoch et al. |
| 2004/0235808 | A1 | 11/2004 | Wang |
| 2005/0003475 | A1 | 1/2005 | Foster et al. |
| 2005/0136004 | A1 | 6/2005 | Xu et al. |
| 2005/0143333 | A1 | 6/2005 | Richards et al. |
| 2006/0142550 | A1 | 6/2006 | Chang |
| 2006/0177447 | A1 | 8/2006 | Xu |
| 2006/0269551 | A1 | 11/2006 | Thompson et al. |

OTHER PUBLICATIONS

Goffe et al. Etanercept: An overview. J Am Acad Dermatol., Aug. 2003; 49(2 Suppl):S105-11.*

Hsu Y.H. et al., "Function of Interleukin-20 as a proinflammatory molecule in rheumatoid and experimental arthritis", Arthritis and Rheumatism, vol. 54(9), pp. 2722-2733 (Sep. 2006).
Hsieh M.Y. et al., "Interleukin-20 promotes angiogenesis in a direct and indirect manner", Genes and Immunity, vol. 7(3), pp. 234-242 (Apr. 2006).
Wei C.C. et al., "IL-20: Biological functions and clinical implications", Journal of Biomedical Science, vol. 13(5), pp. 601-612 (May 16, 2006).
Sabat R. et al., "IL-19 and IL-20: Two novel cytokines with importance in inflammatory diseases", Expert Opinion on Therapeutic Targets, vol. 11(5), pp. 601-612 (May 2007).
Wei C.C. et al., "Detection of IL-20 and its receptors on psoriatic skin", *Clinical Immunology*, vol. 117(1), pp. 65-72 (Oct. 2005).
Chen, W-Y et al. (2009) "IL-20 is Regulated by Hypoxia-inducible Factor and Up-Regulated After Experimental Ischemic Stroke," *Journal of Immunology* 182:5003-5012.
GenBank Accession No. AAK84423.1, last updated Aug. 9, 2001, located at http://www.ncbi.nim.nih.gov/protein/15128211, last visited on Jan. 14, 2010, one page.
Hunt, D.W.C. et al. (Sep./Oct. 2006), "Ultraviolet B Light Stimulates Interleukin-20 Expression by Human Epithelial Keratinocytes," *Photochemistry and Photobiology* 82:1292-1300.
International Search Report mailed on Dec. 19, 2007, for PCT Application No. PCT/US06/46802, filed on Dec. 7, 2006, five pages.
International Search Report mailed on Feb. 18, 2010, for PCT Application No. PCT/US2009/059872, filed on Oct. 7, 2009, five pages.
International Search Report mailed on Feb. 24, 2010, for PCT Application No. PCT/US09/59865, filed on Oct. 7, 2009, five pages.
Mayo Clinic, (Jul. 8, 2008), "Stroke, Treatment and Drugs" located at http://www.MayoClinic.com, last visited on Sep. 29, 2009, three pages.
Mayo Clinic, (2001-2009), "Stroke," located at http://www.MayoClinic.com, last visited on Sep. 29, 2009, two pages.
Written Opinion mailed on Dec. 19, 2007, for PCT Application No. PCT/US06/46802, filed on Dec. 7, 2006, four pages.
Written Opinion mailed on Feb. 18, 2010, for PCT Application No. PCT/US2009/059872, filed on Oct. 7, 2009, six pages.
Written Opinion mailed on Feb. 24, 2010, for PCT Application No. PCT/US09/59865, filed on Oct. 7, 2009, five pages.

* cited by examiner

*Primary Examiner* — Dong Jiang
(74) *Attorney, Agent, or Firm* — Wolf, Greenfield & Sacks, P.C.

(57) ABSTRACT

Treatment of rheumatoid arthritis and osteoporosis using an anti-IL-20 antibody 7E, and optionally, in combination with an etanercept polypeptide.

16 Claims, 2 Drawing Sheets

USE OF ANTI-IL-20 ANTIBODY FOR TREATING RHEUMATOID ARTHRITIS

CROSS-REFERENCE TO RELATED APPLICATIONS

This application is a divisional of U.S. patent application Ser. No. 12/246,715, filed Oct. 7, 2008, now U.S. Pat. No. 7,837,994. Content of this prior application is herein incorporated herein by reference in its entirety.

BACKGROUND OF THE INVENTION

IL-20, a member of the IL-10 family, is a proinflammatory cytokine involved in the pathogenesis of various inflammation-associated diseases, e.g., rheumatoid arthritis and osteoporosis.

Rheumatoid arthritis, the most common inflammatory arthritis, is characterized by infiltration of mononuclear phagocytes, lymphocyts, and neutrophils into synovial membranes and resultant intense inflammation in synovial joints. Recent studies show that a number of cytokines and chemokines, e.g., members of the IL-10 family, play important roles in the development and progression of this disease.

Osteoporosis is a disease characterized by low bone mass and loss of bone tissue, resulting in weak and fragile bones. Net bone loss can be induced by various factors, e.g., low levels of estrogen, inadequate up take of calcium and vitamin D, and inflammation.

SUMMARY OF THE INVENTION

The present invention provides a method of treating rheumatoid arthritis or osteoporosis by administering to a subject in need of the treatment an effective amount of an anti-IL-20 antibody 7E. In one example, the anti-IL-20 antibody 7E is an antibody containing the heavy chain and light chain variable regions of mAb 7E, which is produced by a hybridoma cell line deposited with the American Type Culture Collection as Deposit Number PTA-8687. Examples of this antibody include, but are not limited to, mAb 7E, a functional fragment thereof (such as F(ab')$_2$, Fab), a single-chain antibody, or a chimeric antibody. In another example, the anti-IL-20 antibody 7E is a humanized antibody of mAb 7E.

In the above-described method, the subject preferably is further administered with an effective amount of an etanercept polypeptide. In one example, the etanercept polypeptide is a fusion protein containing human soluble TNF receptor (SEQ ID NO:5 shown below) and the Fc component of human IgG1 (i.e., Etanercept).

The term "treating" as used herein refers to the application or administration of a composition including one or more active agents to a subject, who has rheumatoid arthritis or osteoporosis, a symptom of either diseases, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

Also within the scope of this invention is use of anti-IL-20 antibody 7E, preferably with an etanercept polypeptide, for treating rheumatoid arthritis and osteoporosis or for the manufacture of a medicament for these treatments.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The drawings are first described.

DETAILED DESCRIPTION OF THE INVENTION

Described herein is use of an anti-IL-20 antibody 7E for treating rheumatoid arthritis and osteoporosis.

The term "anti-IL-20 antibody 7E" refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. on Oct. 16, 2007 and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent request of the deposit.

A "functional equivalent" of mAb 7E is an antibody that (1) specifically binds to human IL-20, and (2) contains a heavy chain variable region ($V_H$) at least 70% (e.g., 80%, 90%, or 95%) identical to that of mAb 7E (shown below as SEQ ID NO: 2, encoded by the nucleotide sequence of SEQ ID NO:1) and a light chain variable region ($V_L$) at least 70% (e.g., 80%, 90%, or 95%) identical to that of mAb 7E (shown below as SEQ ID NO: 4, encoded by the nucleotide sequence of SEQ ID NO:3). See U.S. patent application Ser. No. 11/763,812.

```
Nucleotide sequence (SEQ ID NO: 1) and amino acid sequence
(SEQ ID NO: 2) of mAb 7E heavy chain variable region
gaa ttg aag ctt gag gag tct gga gga ggc ttg gtg cag cct gga    45
 E   L   K   L   E   E   S   G   G   G   L   V   Q   P   G    15 gga tcc atg aaa ctc tct tgt gct gcc tct gga ttc act ttt agt    90
 G   S   M   K   L   S   C   A   A   S   G   F   T   F   S    30 gac gcc tgg atg gac tgg gtc cgc cag tct cca gag aag ggg ctt   135
 D   A   W   M   D   W   V   R   Q   S   P   E   K   G   L    45
```

-continued

```
gag tgg att gct gaa att aga agc aaa gct aat aat tat gca aca  180
 E   W   I   A   E   I   R   S   K   A   N   N   Y   A   T   60 tac ttt gct gag tct gtg aaa ggg agg ttc acc atc tca aga gat  215
 Y   F   A   E   S   V   K   G   R   F   T   I   S   R   D   75 gat tcc aaa agt ggt gtc tac ctg caa atg aac aac tta aga gct  270
 D   S   K   S   G   V   Y   L   Q   M   N   N   L   R   A   90 gag gac act ggc att tat ttc tgt acc aag tta tca cta cgt tac  315
 E   D   T   G   I   Y   F   C   T   K   L   S   L   R   Y   105 tgg ttc ttc gat gtc tgg ggc gca ggg acc acg gtc acc gtc tcc  360
 W   F   F   D   V   W   G   A   G   T   T   V   T   V   S   120 tca                                                          363
 S                                                           121

Nucleotide sequence (SEQ ID NO: 3) and amino acid sequence
(SEQ ID NO: 4) of mAb 7E light chain variable region
gat ttt gtg atg acc cag act cca ctc act ttg tcg gtt acc att   45
 D   F   V   M   T   Q   T   P   L   T   L   S   V   T   I   15 gga caa cca gcc tcc atc tct tgc aag tca agt cag agc ctc ttg   90
 G   Q   P   A   S   I   S   C   K   S   S   Q   S   L   L   30 gat agt gat gga aag aca tat ttg aat tgg ttg tta cag agg cca  135
 D   S   D   G   K   T   Y   L   N   W   L   L   Q   R   P   45 ggc cag tct cca aag cac ctc atc tat ctg gtg tct aaa ctg gac  180
 G   Q   S   P   K   H   L   I   Y   L   V   S   K   L   D   60 tct gga gtc cct gac agg ttc act ggc agt gga tca ggg acc gat  215
 S   G   V   P   D   R   F   T   G   S   G   S   G   T   D   75 ttc aca ctg aga atc agc aga gtg gag get gag gat ttg gga gtt  270
 F   T   L   R   I   S   R   V   E   A   E   D   L   G   V   90 tat tat tgc tgg caa agt aca cat ttt ccg tgg acg ttc ggt gga  315
 Y   Y   C   W   Q   S   T   H   F   P   W   T   F   G   G   105 ggc acc aag ctg gaa atc aaa cgg                              339
 G   T   K   L   E   I   K   R                               113
```

As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alighments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

A functional equivalent of mAb 7E can be its fragment generated by enzyme digestion, e.g., Fab or F(ab')$_2$. It also can be a genetically engineered antibody containing the $V_H$ and $V_L$ regions of mAb 7E. Examples of such antibodies include, but are not limited to, a single-chain antibody in which the $V_H$ and $V_L$ of mAb 7E are covalently fused via a linker (e.g., a peptide linker), and a mouse-human chimeric antibody, in which the $V_H$ and $V_L$ of mAb 7E are respectively linked with the constant regions of the heavy and light chains of a human IgG.

The functional equivalent can also be a humanized antibody. The term "humanized antibody" refers to a non-human antibody, in which the frame regions (FRs) of its $V_H$ and $V_L$ and the constant regions, if any, are replaced with FRs and the constant regions of a human antibody. Further, the mAb 7E functional equivalent can be generated by introducing mutations in the FRs of either $V_H$ or $V_L$. It is well known that complementarity-determining regions (CDRs) of an antibody determine its antigen specificity. Accordingly, mutations in FRs normally would not affect antibody specificity. The CDRs and FRs of an antibody can be determined based on the amino acid sequences of its $V_H$ and $V_L$. See www.bioinf.org.uk/abs. The binding-specificity of the functional equivalents described herein can be examined using methods known in the art, e.g., ELISA or western-blot analysis.

MAb 7E and its functional equivalents can be prepared via conventional methods, e.g., by purifying the antibody secreted from the hybridoma cells described above, or by genetic engineering.

The anti-IL-20 antibody 7E described herein can be used alone, or in combination with an etanercept polypeptide, for treating rheumatoid arthritis or osteoporosis. The term "etanercept polypeptide" refers to a fusion protein containing a soluble receptor of tumor necrosis factor (TNF) and the Fc component of an immunoglobulin. In one example, the soluble TNF receptor is a human soluble TNF receptor having the amino acid sequence SEQ ID NO:5 shown below and its functional equivalent, i.e., a polypeptide having an amino acid sequence at least 85% (e.g., 90%, 95%, or 98%) identical to SEQ ID NO:5 and capable of binding to human TNF. The etanercept polypeptide can be made by conventional recombinant technology.

Amino acid sequence of human soluble TNF receptor
(SEQ ID NO: 5)
    aqvaft pyapepgstc rlreyydqta qmccskcspg qhakvfctkt sdtvcdsced stytqlwnwv peclscgsrc ssdqvetqac treqnrictc rpgwycalsk qegcrlcapl rkcrpgfgva rpgtetsdvv ckpcapgtfs nttsstdicr phqic When used for treating rheumatoid arthritis or osteoporosis, the antibody described herein, optionally combined with an etanercept polypeptide, can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

Conventional methods, known to those of ordinary skill in the art of medicine, can be used to administer the anti-IL-20-antibody-containing pharmaceutical composition to the subject, depending upon the type of disease to be treated or the site of the disease. For treating rheumatoid arthritis, the antibody-containing composition can be delivered directly to synovial joints via injection. This composition can also be administered via other conventional routes, e.g., subcutaneous. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLE 1

Treating Rheumatoid Arthritis with Monoclonal Antibody 7E (mAb 7E)

Rats having collagen-induced arthritis (CIA) is a well-developed animal model for studying human rheumatoid arthritis. This model was employed in this study to examine the efficacy of mAb 7E for treating this disease.

CIA was induced in eight-week-old male Sprague-Dawley rats as follows. The rats were immunized initially by intradermal injection (in the dorsum) of 200 µl emulsion containing Freund's complete adjuvant, 4 mg/ml heat-killed *Mycobacterium tuberculosis* (Arthrogen-CIA; Chondrex, Redmond, Wash.), and bovine type II collagen (CII; 2 mg/ml dissolved in 0.05 M acetic acid) at a ratio of 1:1:1 (v/v/v). Eight days later, the rats were then injected subcutaneously with 100 µl of the just-described emulsion in the roots of the tails to boost their immune responses. CIA was observed in these rats between day 11 and day 13 after the initial immunization.

The following four groups of rats (n=5) were subjected to this study:
  Group (1): healthy rats
  Group (2): CIA rats, as described above, administered with PBS (s.c.) one week after CIA onset,
  Group (3): CIA rats administered with mAb 7E (3 mg/kg, s.c.) one week after CIA onset, and
  Group (4): Etanercept (Enebrel; Wyeth, USA, 3 mg/kg, s.c.) one week after CIA onset.

Hind-paw thickness of each treated rat was measured with a caliper. All raw results obtained from this study were subjected to statistical analysis using statistical software Prism 4.0; GraphPad Software, San Diego, Calif., USA. The Kruskal-Wallis test was used to compare the thickness of the hind paws. P-values<0.05 were considered significant.

As shown in Table 1 below, mAb 7E significantly reduced hind-paw thickness in CIA rats (p<0.05) and its efficacy was close to that of Etanercept, a commercially available anti-rheumatoid arthritis drug (see Mihara et al., *Br J Pharmacol.*, 2008, 154:153-164). This result indicates that, like Etanercept, mAb 7E is also effective in treating rheumatoid arthritis.

TABLE 1

Hind-Paw Thickness of Control and Treated Rats

| GROUP | Median Hind-Paw Thickness | 25th-75th Percentiles |
| --- | --- | --- |
| 1 (health control) | 0.53 cm | 0.52-0.54 cm |
| 2 (PBS-treated) | 1.05 cm | 1.02-1.13 cm |
| 3 (mAb 7E-treated) | 0.84 cm | 0.72-0.93 cm |
| 4 (Etanercept-treated) | 0.86 cm | 0.78-0.91 cm |

Next, the effect of mAb 7E in reducing levels of inflammatory mediators in synovial tissue was examined as follows. The synovial tissues surrounding the knee joints in the treated CIA rats were isolated and suspended in a PBS solution. The tissues were then homogenized, centrifuged at 3000 rpm for 10 min at 4° C., and the supernatants thus obtained were stored at −80° C., ready for analysis. The levels of TNF-α, IL-1β (TNF-α and IL-1β kits; R&D Systems, Minneapolis, Minn.), and IL-20 (IL-20 kit; PeproTech Asia/CytoLab, Rehovot, Israel) were evaluated using a sandwich ELISA assay according to the manufacturer's instructions. It is known in the art that the levels of all these inflammatory mediators are elevated in CIA rats.

Results thus obtained indicate that mAb 7E and Etanercept significantly reduced the levels of TNF-α, IL-1β, and IL-20 as compared with mIgG. More specifically, while in mIgG-treated CIA rats, the levels of TNF-α, IL-1β, and IL-20 in synovial tissues were much higher than those in the synovial tissues of healthy control rats, they were significantly reduced in CIA rats treated with mAb 7E or Etanercept.

EXAMPLE 2

Treating Rheumatoid Arthritis with Both mAb 7E and Etanercept

CIA was induced in rats following the method described in Example 1. The CIA rats were randomly assigned to five groups (n=9 in each group) and treated as follows three times per week after CIA onset:

Group 1: PBS

Group 2: mouse IgG, obtained from Chemicon International, Inc., Temecula, Calif., USA, Group 3: Etanercept (6 mg/kg, s.c.), Group 4: mAb 7E (6 mg/kg, s.c.), and Group 5: mAb 7E (3 mg/kg, s.c.) and Etanercept (3 mg/kg, s.c.).

First, the thickness of hind-paw of each treated rats was examined following the methods described in Example 1 above. The combined treatment of mAb 7E and Etanercept showed significantly higher effect in reducing hind-paw thickness as compared to the individual treatment of mAb 7E and Etanercept.

Next, the severity of CIA in each hind paw of the rats was monitored and scored, following the method described in Hsu et al., *Arthritis Rheum.* 2006, 54:2722-2733. Generally, if a rat has a severity score higher than 3, that rat is considered as having severe swelling in its hind paw. The Kruskal-Wallis test was applied to compare the severity scores obtained from different groups to assess whether the results were statistical significant. As shown in Table 2 below, the median severity score of rats treated with both mAb 7E and Etanercept was much lower than that of rats treated with mAb 7E alone or with Etanercept alone. These results were statistically significant (P<0.05).

TABLE 2

Severity Score of Healthy and CIA Rats Treated with Various Agents

| GROUP | Median Severity Score | 25th-75th Percentiles |
| --- | --- | --- |
| Healthy controls | 0.02 | 0.0-0.4 |
| Group 1 (PBS) | 4.2 | 3.9-4.5 |
| Group 2 (mIgG) | 4.0 | 3.5-4.2 |
| Group 3 (mAb 7E) | 2.0 | 0.5-3.1 |
| Group 4 (Etanercept) | 2.1 | 0.7-3.6 |
| Group 5 (mAb 7E + Etanercept) | 0.9 | 0.0-2.2 |

Figure 1:
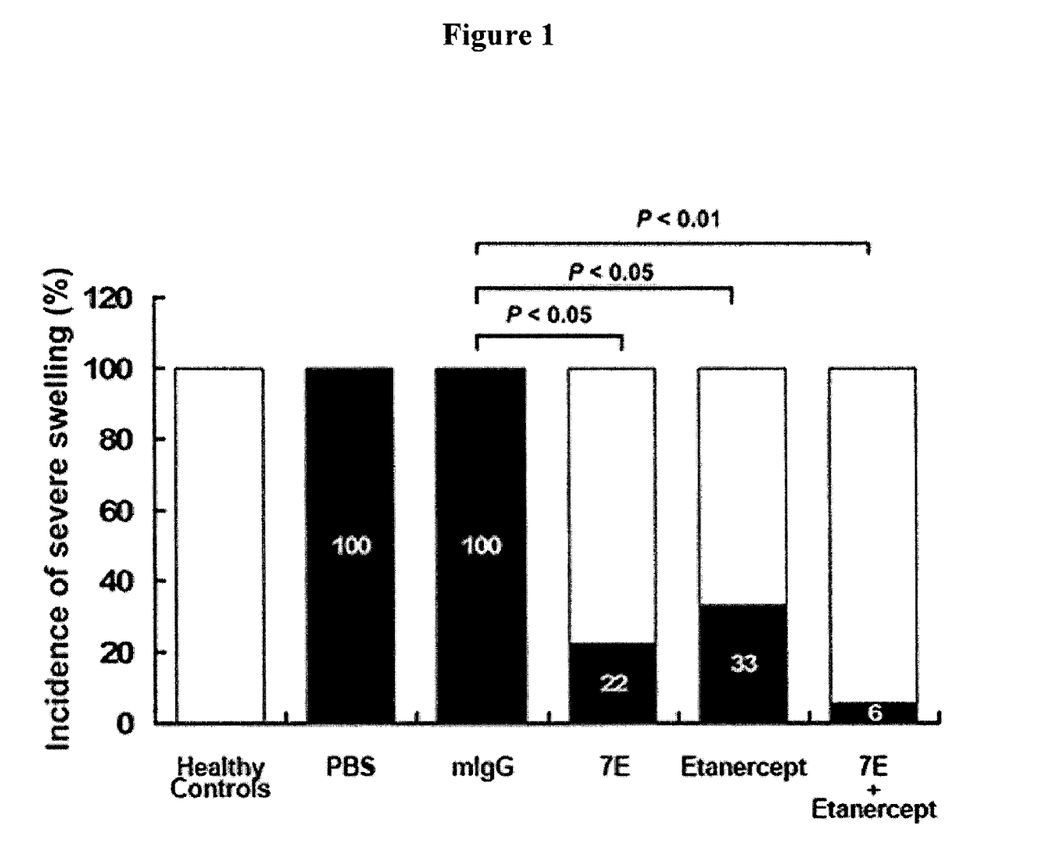
FIG. 1 is a chart showing the incidence of severe hind paw swelling in healthy rats and collagen-induced-arthritic rats treated with PBS, mIgG, mAb 7E, Etanercept, or both mAb 7E and Etanercept.

The presence of severe hind-paw swelling was then examined in each treated CIA rat and the results were shown in FIG. 1. Unexpectedly, while the incidences of severe swelling in the CIA rats treated with mAb 7E and Etanercept, individually, were reduced from 100% to 22% and from 100% to 33%, respectively, the incidence of severe swelling in the CIA rats treated with both mAb 7E and Etanercept reduced from 100% to only 6%. These results, which were statistically significant as analyzed using Fisher's exact test, indicate that the combined treatment of mAb 7E and Etanercept is much more efficient than the individual treatment of mAb 7E or Etanercept.

In addition, the severity of bone damage in the treated CIA rats was examined twenty-five days after the initial immunization with bovine collagen via radio imaging. Severe bone damage was observed in hind-paw joints in the CIA rats treated with PBS and mIgG (i.e., the rats of group 1 and group 2). Surprisingly, the severity of local ankle bone damage was relatively mild in the CIA rats treated with mAb 7E, Etanercept, or the combination thereof (rats of groups 3-5). The differences between groups 1 and 2 rats and groups 3-5 rats were statistically significant (P<0.01-0.05). These results further confirm that mAb 7E alleviated bone damage in CIA rats as efficiently as Etanercept and the combined treatment of mAb 7E and Etanercept was much more efficient than the corresponding individual treatment.

Further, a microcomputed tomographic analysis, using a 1076 microCT-40 system (Skyscan, Aartselaar, Belgium) equipped with a high resolution, low-dose X-ray scanner, was performed to assess the efficacy of mAb 7E alone and its combination with Etanercept in protecting bone destruction in CIA rats. The X-ray tube in the scanner was operated with photon energy of 48 kV, current of 200 uA, and exposure time of 1180 ms through a 0.5-mm-thick filter. The image pixel size was 17.20 um, and the scanning time was approximately 15 min. After standardized reconstruction of the scanned images, the data sets for each tibia sample were resampled with software (CTAn; Skyscan) to orient each sample in the same manner. Consistent conditions such as thresholds were applied throughout all analyses. Bone mineral density, a three-dimensional bone characteristic parameter, was analyzed in 50 consecutive slices. The results were calculated as a percentage versus values relative to an mIgG control.

The tibias obtained from the CIA rats treated with PBS and mIgG showed prominent bone damage compared to the intact joints found in healthy controls. The CIA rats treated with mAb 7E displayed alleviated bone loss compared to the rats treated with mIgG. In the rats treated with both mAb 7E and Etanercept, the bone loss was even less severe relative to the rats treated with either mAb or Etanercept alone.

The bone mineral density, a quantitative parameter for assessing disease severity, was measured in each treated CIA rat as described above. mAb 7E treatment in CIA rats significantly inhibited bone loss as compared to the mIgG-treated CIA rats (P<0.05). The protective effects were drastically increased in the CIA rats treated with both mAb 7E and Etanercept (P<0.01). The microCT result supported the radiological data from their ankle joints. These results provided evidence that mAb 7E not only reduced the severity of arthritis but also inhibited bone loss.

Figure 2:
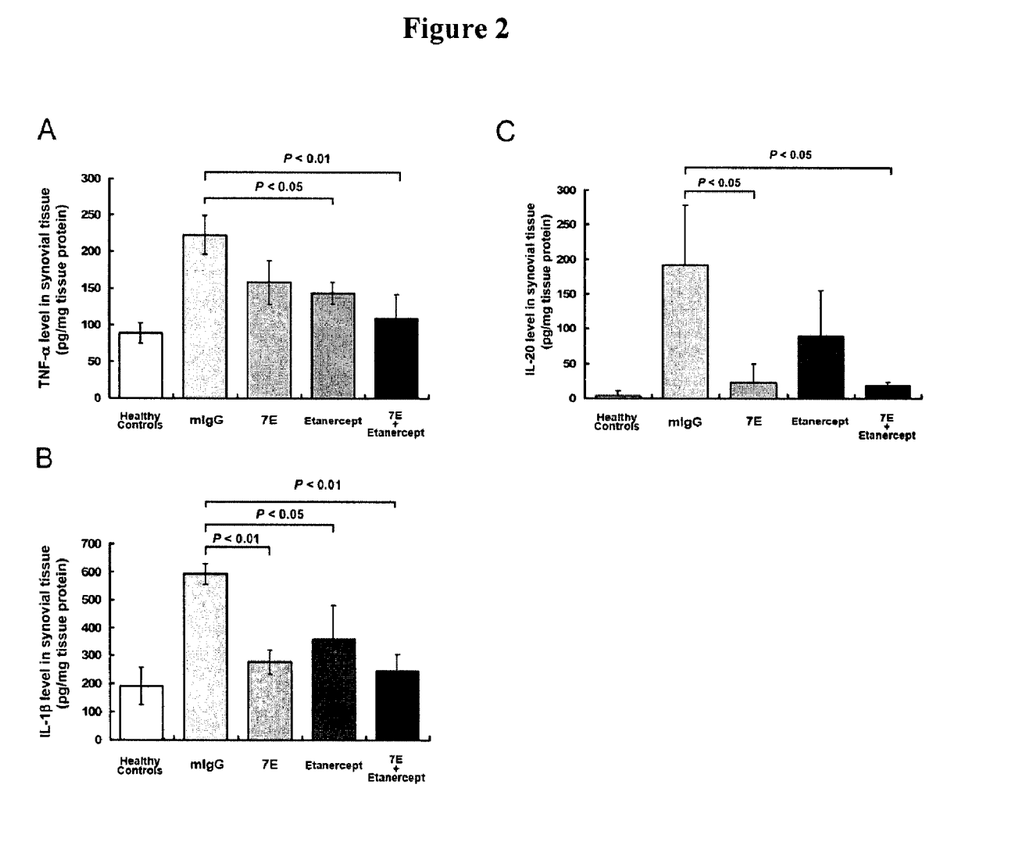
FIG. 2 is a number of charts showing the levels of TNF-α, IL-20, and IL-1β in healthy rats and in collagen-induced-arthritic rats treated with mIgG, mAb 7E, Etanercept, or both mAb 7E and Etanercept.

Finally, the expression levels of TNF-$\alpha$, IL-1$\beta$, and IL-20 were examined in the CIA rats treated with both mAb 7E and Etanercept and the results thus obtained showed that these cytokines were significantly decreased. See FIG. 2.

In sum, the results described above demonstrate that mAb 7E is effective in treating CIA by both reducing severity of arthritis and inhibiting bone loss. These results also indicate that the combined effect of mAb 7E and Etanercept is significantly higher than the individual effect of either mAb 7E or Etanercept.

EXAMPLE 3

Treating Osteoporosis with mAb 7E

Fourteen-week-old female BALB/C mice (Laboratory Animal Center, National Cheng Kung University, Tainan, Taiwan) were housed in an environmentally controlled laboratory upon arrival and acclimatized for 4 days. Animals were allocated in polycarbonate cages (3 per cage) in a temperature/humidity controlled room (20-25° C. and 40-45%). The Light:dark cycle was 12-h light:12-h dark, and feed and water were supplied free to access. The animals were either dorsal ovariectomized (OVX) or falsely operated (Sham controls) under general anesthesia by using pentobarbital (50 mg/kg body weight; Sigma-Aldrich, St. Louis, Mo.). In Sham controls, bilateral ovaries were exposed and then closed with skin suture not removed. The mice were recovered for a week after OVX or control surgery and then randomly assigned to six groups:

Group 1: Sham controls (n=5),

Group 2: OVX mice with no further treatment (n=5),

Group 3: OVX mice treated with 17$\beta$-estradiol (Sigma-Aldrich, St. Louis, Mo., 10 µg/kg/day, n=6), Group 4: OVX mice treated with mIgG (Chemicon International, Inc., Temecula, Calif., USA, 3 mg/kg/three days, n=7)),
Group 5: OVX mice treated with mAb 7E (3 mg/kg/three days, n=5), and
Group 6: OVX mice treated with mAb 7E (6 mg/kg/three days, n=5).

The dosage of 17β-estradiol treatment used as a positive control are based on previous protocols known to be effective in treating OVX mice. See Cano et al., *Osteoporos Int.* 2008 June; 19(6):793-800.

The mice of all groups were sacrificed 2 months later. The tibia of each mouse was aseptically collected, cleaned to remove adherent soft tissues, and deposited in a tube filled with 3.7% formalin. It was then subjected to Microcomputed tomography and bone mineral density analysis following the methods described in Example 2 above.

The results obtained from this study show that the levels of bone damage in Groups 2 and 3 (untreated or treated with mIgG) were much greater than those in Groups 4-6 (treated with 3 mg/kg mAb 7E, 6 mg/kg mAb 7E, and 17β-estradiol), indicating that, like 17β-estradiol, mAb 7E also reduced bone loss in OVX mice. Further, the bone mineral densities in mAb 7E-treated and 17β-estradiol-treated OVX mice were much higher than those in Sham controls and in mIgG-treated mice. Taken together, these results demonstrate that mAb 7E is effective in treating osteoporosis by reducing bone loss.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating rheumatoid arthritis, the method comprising administering to a subject in need thereof an effective amount of an anti-IL-20 antibody and an effective amount of a fusion protein comprising a soluble receptor of a tumor necrosis factor (TNF) and the Fc component of an immunoglobulin, wherein the anti-IL-20 antibody contains a $V_H$ region including all of the complementarity-determining regions in the $V_H$ of mAb7E and a $V_L$ region including all of the complementarity-determining regions in the $V_L$ of mAb7E, mAb7E being produced by the hybridoma cell line deposited with the American Type Culture Collection as Deposit Number PTA-8687.

2. The method of claim 1, wherein the anti-IL-20 antibody is an antibody containing the $V_H$ and $V_1$ regions of mAb 7E.

3. The method of claim 2, wherein the anti-IL-20 antibody is mAb 7E.

4. The method of claim 2, wherein the anti-IL-20 antibody is an antigen-binding fragment of mAb 7E.

5. The method of claim 4, wherein the antigen-binding fragment is a Fab or F(ab')$_2$ fragment.

6. The method of claim 2, wherein the anti-IL-20 antibody is a single chain antibody.

7. The method of claim 2, wherein the anti-IL-20 antibody is a chimeric antibody.

8. The method of claim 1, wherein the anti-IL-20 antibody is a humanized antibody.

9. The method of claim 1, wherein the fusion protein comprises a soluble human TNF receptor having the amino acid sequence of SEQ ID NO:5.

10. The method of claim 9, wherein the anti-IL-20 antibody is an antibody containing the $V_H$ and $V_L$ regions of mAb 7E.

11. The method of claim 10, wherein the anti-IL-20 antibody is an antigen-binding fragment of mAb 7E.

12. The method of claim 11, wherein the antigen-binding fragment is a Fab or F(ab')$_2$ fragment.

13. The method of claim 10, wherein the anti-IL-20 antibody is a single chain antibody.

14. The method of claim 10, wherein the anti-IL-20 antibody is a chimeric antibody.

15. The method of claim 9, wherein the anti-IL-20 antibody is a humanized antibody.

16. The method of claim 9, wherein the anti-IL-20 antibody is mAb 7E.

* * * * *

SEQUENCE LISTING

```
<160> NUMBER OF SEQ ID NOS: 5

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 1 gaa ttg aag ctt gag gag tct gga gga ggc ttg gtg cag cct gga gga        48
Glu Leu Lys Leu Glu Glu Ser Gly Gly Gly Leu Val Gln Pro Gly Gly
1               5                   10                  15 tcc atg aaa ctc tct tgt gct gcc tct gga ttc act ttt agt gac gcc        96
Ser Met Lys Leu Ser Cys Ala Ala Ser Gly Phe Thr Phe Ser Asp Ala
            20                  25                  30 tgg atg gac tgg gtc cgc cag tct cca gag aag ggg ctt gag tgg att       144
Trp Met Asp Trp Val Arg Gln Ser Pro Glu Lys Gly Leu Glu Trp Ile
        35                  40                  45 gct gaa att aga agc aaa gct aat aat tat gca aca tac ttt gct gag       192
Ala Glu Ile Arg Ser Lys Ala Asn Asn Tyr Ala Thr Tyr Phe Ala Glu
    50                  55                  60 tct gtg aaa ggg agg ttc acc atc tca aga gat gat tcc aaa agt ggt       240
Ser Val Lys Gly Arg Phe Thr Ile Ser Arg Asp Asp Ser Lys Ser Gly
65                  70                  75                  80 gtc tac ctg caa atg aac aac tta aga gct gag gac act ggc att tat       288
Val Tyr Leu Gln Met Asn Asn Leu Arg Ala Glu Asp Thr Gly Ile Tyr
                85                  90                  95 ttc tgt acc aag tta tca cta cgt tac tgg ttc ttc gat gtc tgg ggc       336
Phe Cys Thr Lys Leu Ser Leu Arg Tyr Trp Phe Phe Asp Val Trp Gly
            100                 105                 110 gca ggg acc acg gtc acc gtc tcc tca                                   363
Ala Gly Thr Thr Val Thr Val Ser Ser
        115                 120

<210> SEQ ID NO 2
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
            100                 105                 110

Ala Gly Thr Thr Val Thr Val Ser Ser
            115                 120

<210> SEQ ID NO 3
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 3 gat ttt gtg atg acc cag act cca ctc act ttg tcg gtt acc att gga       48
Asp Phe Val Met Thr Gln Thr Pro Leu Thr Leu Ser Val Thr Ile Gly
1               5                   10                  15 caa cca gcc tcc atc tct tgc aag tca agt cag agc ctc ttg gat agt       96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct      144
Asp Gly Lys Thr Tyr Leu Asn Trp Leu Leu Gln Arg Pro Gly Gln Ser
        35                  40                  45 cca aag cac ctc atc tat ctg gtg tct aaa ctg gac tct gga gtc cct      192
Pro Lys His Leu Ile Tyr Leu Val Ser Lys Leu Asp Ser Gly Val Pro
    50                  55                  60 gac agg ttc act ggc agt gga tca ggg acc gat ttc aca ctg aga atc      240
Asp Arg Phe Thr Gly Ser Gly Ser Gly Thr Asp Phe Thr Leu Arg Ile
65                  70                  75                  80 agc aga gtg gag gct gag gat ttg gga gtt tat tat tgc tgg caa agt      288
Ser Arg Val Glu Ala Glu Asp Leu Gly Val Tyr Tyr Cys Trp Gln Ser
                85                  90                  95 aca cat ttt ccg tgg acg ttc ggt gga ggc acc aag ctg gaa atc aaa      336
Thr His Phe Pro Trp Thr Phe Gly Gly Gly Thr Lys Leu Glu Ile Lys
            100                 105                 110 cgg                                                                  339
Arg

<210> SEQ ID NO 4
<211> LENGTH: 113
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

Arg

<210> SEQ ID NO 5
<211> LENGTH: 161
<212> TYPE: PRT
<213> ORGANISM: Homo sapiens

<400> SEQUENCE: 5

Ala Gln Val Ala Phe Thr Pro Tyr Ala Pro Glu Pro Gly Ser Thr Cys
1               5                   10                  15

Arg Leu Arg Glu Tyr Tyr Asp Gln Thr Ala Gln Met Cys Cys Ser Lys
            20                  25                  30

Cys Ser Pro Gly Gln His Ala Lys Val Phe Cys Thr Lys Thr Ser Asp
        35                  40                  45

Thr Val Cys Asp Ser Cys Glu Asp Ser Thr Tyr Thr Gln Leu Trp Asn
    50                  55                  60

Trp Val Pro Glu Cys Leu Ser Cys Gly Ser Arg Cys Ser Ser Asp Gln
65                  70                  75                  80

Val Glu Thr Gln Ala Cys Thr Arg Glu Gln Asn Arg Ile Cys Thr Cys
                85                  90                  95

Arg Pro Gly Trp Tyr Cys Ala Leu Ser Lys Gln Glu Gly Cys Arg Leu
            100                 105                 110

Cys Ala Pro Leu Arg Lys Cys Arg Pro Gly Phe Gly Val Ala Arg Pro
            115                 120                 125

Gly Thr Glu Thr Ser Asp Val Val Cys Lys Pro Cys Ala Pro Gly Thr
        130                 135                 140

Phe Ser Asn Thr Thr Ser Ser Thr Asp Ile Cys Arg Pro His Gln Ile
145                 150                 155                 160

Cys
```